US010450545B2

(12) United States Patent
Pan et al.

(10) Patent No.: US 10,450,545 B2
(45) Date of Patent: Oct. 22, 2019

(54) MICROFLUIDIC CHIPS FOR ACQUIRING SPERMS WITH HIGH MOTILITY, PRODUCTIONS AND APPLICATIONS THEREOF

(75) Inventors: Richard Li-Chern Pan, Taipei (TW); Fan-Gang Tseng, Hsinchu (TW); Jen-Kuei Wu, Hsinchu (TW); Peng-Chun Chen, Hsinchu (TW)

(73) Assignees: NATIONAL TSING HUA UNIVERSITY, Hsinchu (TW); TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 14/344,866

(22) PCT Filed: Sep. 14, 2012

(86) PCT No.: PCT/US2012/055534
§ 371 (c)(1),
(2), (4) Date: Jul. 10, 2014

(87) PCT Pub. No.: WO2013/040428
PCT Pub. Date: Mar. 21, 2013

(65) Prior Publication Data
US 2014/0315281 A1    Oct. 23, 2014

Related U.S. Application Data

(60) Provisional application No. 61/534,464, filed on Sep. 14, 2011.

(51) Int. Cl.
*C12N 5/076* (2010.01)
*C12M 3/00* (2006.01)
(Continued)

(52) U.S. Cl.
CPC ............ *C12N 5/061* (2013.01); *B01L 3/5027* (2013.01); *C12M 21/06* (2013.01); *C12M 23/16* (2013.01);
(Continued)

(58) Field of Classification Search
CPC ....... B01L 2300/028; B01L 2300/0816; B01L 2300/087; B01L 2400/084; B01L 3/5027;
(Continued)

(56) References Cited

U.S. PATENT DOCUMENTS 5,296,375 A    3/1994  Kricka et al.
6,150,119 A *  11/2000 Kopf-Sill ............ B01F 13/0071
                                                    204/400
(Continued)

FOREIGN PATENT DOCUMENTS

WO    WO 2004/113877    12/2004

OTHER PUBLICATIONS

Office action dated Apr. 18, 2016 for the Taiwan counterpart application 101133928.
(Continued)

*Primary Examiner* — Samuel P Siefke
(74) *Attorney, Agent, or Firm* — WPAT, P.C., Intellectual Property Attorneys; Anthony King

(57) ABSTRACT

This invention relates to microfluidic chips for and their applications in acquiring sperms with high velocity and/or motility. The microfluidic chip comprises an inlet region, a first flow channel, a divergent channel, an optional block structure with rounded corners and one or more outlet region(s). The invention mimics sperm activation process in body and designs a microfluidic chip mimicking the activation process so that higher amount of populations and/or subpopulations of sperms with high motility can be acquired.

14 Claims, 12 Drawing Sheets

(51) Int. Cl.
  *C12M 3/06* (2006.01)
  *B01L 3/00* (2006.01)
  *G01N 33/50* (2006.01)
(52) U.S. Cl.
  CPC .... *G01N 33/5029* (2013.01); *B01L 2300/028* (2013.01); *B01L 2300/087* (2013.01); *B01L 2300/0816* (2013.01); *B01L 2400/084* (2013.01); *B01L 2400/086* (2013.01)
(58) Field of Classification Search
  CPC . B01L 2400/086; C12M 21/06; C12M 23/16; C12N 5/061; G01N 33/5029
  See application file for complete search history.

(56) References Cited

U.S. PATENT DOCUMENTS

| | | | | |
|---|---|---|---|---|
| 9,023,613 | B2* | 5/2015 | Tseng | C12N 5/0612 |
| | | | | 435/2 |
| 2003/0165812 | A1* | 9/2003 | Takayama | B01L 3/502753 |
| | | | | 435/4 |
| 2004/0219507 | A1 | 11/2004 | Abed | |
| 2007/0160503 | A1* | 7/2007 | Sethu | A61M 1/3633 |
| | | | | 422/400 |

OTHER PUBLICATIONS

English translation of the Office action dated Apr. 18, 2016 for the Taiwan counterpart application 101133928.
Search report dated Apr. 18, 2016 for the Taiwan counterpart application 101133928.
English translation of the search report dated Apr. 18, 2016 for the Taiwan counterpart application 101133928.
Office Action and Search report dated Mar. 20, 2016 for the China counterpart application 201280045056.8.
English translation of the Office Action dated Mar. 20, 2016 for the China counterpart application 201280045056.8.
English translation of the Search report dated Mar. 20, 2016 for the China counterpart application 201280045056.8.
European counterpart application 12832184.1 dated Mar. 20, 2015.

* cited by examiner

MICROFLUIDIC CHIPS FOR ACQUIRING SPERMS WITH HIGH MOTILITY, PRODUCTIONS AND APPLICATIONS THEREOF

FIELD OF THE INVENTION

This invention relates to microfluidic chips and methods for sorting and/or activating sperms with high velocity and/or motility. In particular, the microfluidic chip comprises an inlet region, a first flow channel, a divergent channel and one or more outlet region(s).

BACKGROUND OF THE INVENTION

It has been shown that male factor is a contributory cause of infertility in about 40% to 50% of the infertile couples. The overwhelming majority of these infertile and subfertile men are oligospermic and/or asthenospermic (sperm motility is lower than 50%). Management problems exist with respect to these infertile men, as these men may try to be fathers for years without success. With intrauterine placement of the sperm, the pregnancy rates for couples with male factor infertility are only at about 15-20% per cycle. This is in spite of the fact that there is no detectable difference in sperm concentrations and motility among the groups of husbands who do or do not cause pregnancy following intrauterine insemination treatment. Although the pregnancy rates with in vitro fertilization treatment are relatively high, but adequate sperm concentration or sperm motility does not assure the success of pregnancies. There are also men who suffer from unexplained male infertility problems, i.e. sperm with diminished fertility in spite of normal sperm concentrations.

Artificial insemination has become a much more frequent procedure due to a variety of sociological, economic, and perhaps environmental reasons. The number of inseminations worldwide has been increasing, and will likely continue to increase. A number of causes have been cited for this increase. For example, the increased age often lower the probability of fertilization for both men and women. More and more women are also raising children by themselves without a partner, and electing artificial insemination as a means of fertilization. In addition, those that would otherwise not be able to have children, now have a medical option that is relatively affordable. An additional factor may be that the sperm count among males has been declining, making fertilization more difficult. And finally, environmental factors have also been blamed for the decreased fertility of both men and woman.

There are currently a wide variety of artificial insemination methods such as, intracervical, intrauterine (IUI), intratubular and direct intraperitoneal (DIPI) insemination, gamete intrafallopian transfer (GIFT), in vitro fertilization and embryo transfer (IVFET), zygote intrafallopian transfer (such as ZIFT, PROST and TET), peritoneal oocyte and sperm transfer (POST), and sex selection, among others. As technology advances, other methods are certain to follow, however, regardless of the process; high motile sperm are always preferred. And, most of the facilities that perform the insemination do not have the resources to separate motile sperm, requiring a separate visit to facility that possesses the separation means. As an example, the Intrauterine Insemination (IUI) and In Vitro fertilization (IVF) methods attempt to mimic the reproductive process by placing sperm and eggs together in an environment conducive to fertilization, either in the womb or outside the womb. The fertilization process requires the sperm to actively invade the egg and commence fertilization. Motile sperm are much more likely to penetrate the egg.

Human semen is comprised of a heterogeneous cell population with different degrees of maturation, varying in functional quality and fertilizing ability. Ejaculated sperm are not immediately able to fertilize an egg. Rather, they must undergo a process of functional maturation known as "capacitation". "Capacitation" is generally regarded to be a process that results in the acquisition of hyperactivated motility, and the acquisition of the ability to undergo acrosomal exocytosis. Capacitation results in two specific changes in sperm function. First, the sperm head acquires the ability to undergo acrosomal exocytosis in response to physiological ligands such as zona pellucida proteins or progesterone. Second, the flagellum of the sperm acquires a "hyperactivated" pattern of motility.

Fractionation of sperm by a density gradient centrifugation can separate these subpopulations, resulting in a considerable improvement in the quality of sperm recovered in the pellet. Several regions indicate that higher percentages of motile and morphologically normal sperm can be recovered from the pellet, in comparison with lower density fractions. Semen is composed of a heterogeneous population of sperm with varying degrees of structural and functional differentiation and normality. From Percoll gradient, three subsets of sperm (45%; L45), (65%; L65) and (90%; L90) fractions are often adapted when separating high quality sperm from normozoospermic human semen. L45 showed the poorest quality, displaying the smallest percentage of morphologically normal and motile sperm. L65 and L90 showed a time-dependent increment in capacitation-associated tyrosine phosphorylation (M. G. Buffone et al., *Human Reprod* Vol. 19, No. 1 pp 139-146, 2004).

The total number of sperms in one ejaculate is a measure of fertility; however, the percentage of motile sperm is more important, especially when considering alternate reproductive means. According to motility, sperms are categorized as shown in the following table:

| Motility Index | |
|---|---|
| Degree of Motility | Type of Motility |
| 0 | No motility, or movement of tail with no forward progression |
| 1 | 20% or less showing forward progression (sluggish movement) |
| 2 | 20%-50% showing forward progression |
| 3 | 50%-80% showing forward progression |
| 4 | 80%-100% shown forward progression (very rapid movement) |

The percentage of motile sperm showing progressive swimming movements is a measure of the fertility of the sperm sample. The higher the percentage, the higher quality of the sperm sample, and the greater the likelihood that the sample will achieve fertilization. A high quality sperm sample is important for many reasons. The process of artificial insemination is not only costly economically, but is psychologically expensive. Unsuccessful attempts have devastating effects on the patients. Higher quality sperm samples are also important considerations when the sample is subject to freezing or aqueous dilution, because these processes tend to kill or weaken the sample. Thus, only the highest quality sperm may survive the processing procedures to which the sperm are subjected.

Various methods of selecting the more active sperm have been utilized in the past, such as the swim up, swim down and Percoll density gradient centrifugation techniques. Swim-up methods are commonly used to process fresh or frozen specimens for the IUI and IVF procedures. The sperm is placed in a medium and subjected to a centrifuge process. The more motile sperm swim to a level where they can be extracted. Such methods employ multiple tube and centrifugation steps that are time consuming and can lead to a low recovery of motile sperm.

A number of methods exist for assessing motility and number of spermatozoa in a sample. One such method is microscopic analysis, which is typically performed in a hospital or commercial laboratory. More recently, however, a number of proposals have been made for test kits which are intended to simplify detection of spermatozoa. A disadvantage of these test kits is that they do not distinguish between motile and non-motile spermatozoa. This distinction is a most predictive indicator of male infertility.

U.S. Pat. No. 5,427,946 discloses a channeling apparatus, where there are inlet regions, flow channels, and nesting chambers. The sperm sample is applied at the inlet region, and only the motile sperm are capable of reaching the chambers. U.S. Pat. No. 7,179,641 provides an apparatus for separating and detecting motile spermatozoa in a liquid sample, comprises: a separation vessel including (i) an inlet region, (ii) an outlet region arranged to be opened, (iii) a separation medium into which motile spermatozoa in the sample can flow via the inlet region, and (iv) an actuator operable to open the outlet region for allowing the separation medium to flow out of the vessel through the outlet region. These prior art references are not based on the microfluidic techniques.

U.S. Pat. No. 6,929,945 provides a device including a microfluidics structure having a sample reservoir, a downstream collection region and a microchannel extending therebetween. The microchannel is dimensioned to confine sample sperm to single-direction movement within the channel, such that sperm in a semen sample placed in the sample reservoir enter and migrate along the microchannel toward and into the collection region. Brenda et al. provides a self-contained integrated microfluidic system for separating motile sperm from small samples, which comprises two sample inlets, two outlets, sorting channel and a passively driven pumping system that provides a steady flow of liquid. US Patent Publication No. 20100291535 discloses a method using a microfluidic chip to sort high motility sperm. In this prior art reference, sperm and a medium are respectively injected into a microchannel of a microfluidic chip via several inlets. However, the above prior references cannot make a distinguishable sorting to obtain different subpopulations of sperm. That is, the sperms sorted by the above prior references may include high motile sperms, low motile sperms and even no motile sperms. Moreover, the amounts of motile sperms sorted by the above prior art references cannot achieve a satisfied level.

Therefore, there is still a need to develop a device and method to sort not only sperms with higher motility and activity but also with more amounts in the targeted quality as well.

SUMMARY OF THE INVENTION

The invention relates to a microfluidic chip for acquiring sperms with high motility in a sperm sample, which comprises:

(a) an inlet region at one end of the microfluidic chip;
(b) a first flow channel that is in fluidic communication with the inlet region;
(c) a divergent channel, which is arranged at the downstream of the flow channel and in fluidic communication with the flow channel; and
(d) one or more outlet region(s) located at one or both sides of the divergent channel The invention also relates to microfluidic chip for acquiring sperms with high motility in a sperm sample, which comprises:

(a) an inlet region at one end of the microfluidic chip;
(b) a first flow channel that is in fluidic communication with the open region of (a);
(c) a divergent channel, which is arranged at the downstream of the flow channel and in fluidic communication with the flow channel;
(d) one or more outlet region(s) located at one or both sides of the divergent channel;
(e) a second flow channel arranged at the downstream of the divergent channel; and
(f) an outlet region at the opposite end of the inlet region of (a) of the microfluidic chip and in fluidic communication with the second flow channel.

The invention also relates to a method, kit and system of using the microfluidic chip of the invention.

DETAILED DESCRIPTION OF THE INVENTION

Figure 1:
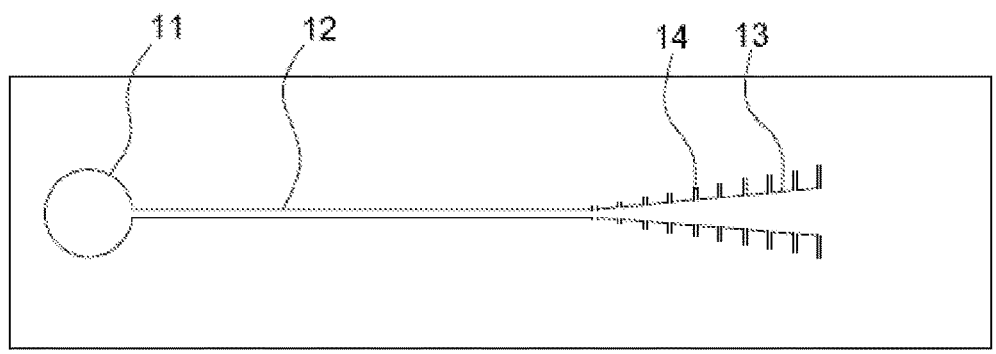
FIG. 1 shows an overall view of the microfluidic chip of the invention comprising an inlet region, first flow channel, a divergent channel and one or more outlet region(s).

The invention provides a microfluidic chip for acquiring populations and/or subpopulations of sperms with high motility and/or activity. The invention mimics sperm activation process in body and designs a microfluidic chip mimicking the activation process so that higher amount of populations and/or subpopulations of sperms with high motility and/or activity can be acquired. The semen may be directly applied to the microfluidic channel without dilution.

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can typically be described in more than one way. Consequently, alternative language and synonyms may be used for any one or more of the terms discussed herein. Synonyms for certain terms are provided. However, a recital of one or more synonyms does not exclude the use of other synonyms, nor is any special significance to be placed upon whether or not a term is elaborated or discussed herein.

The term "microfluidic channel" means a channel having width and depth dimensions that facilitate sperm movement through the channel in a manner similar to the in vivo situation. Typically the microchannel has width and depth dimensions each between about 10 micrometers to 5 mm. The microfluidic channel may be of any cross-sectioned geometry, such as round or rectangular, and up to many cm in length.

The term "flow" means any movement of liquid or solid through a device or in a method of the invention, and encompasses without limitation any fluid stream, and any material moving with, within or against the stream, whether or not the material is carried by the stream. For example, the movement of sperms through a device or in a method of the invention, e.g. through channels of a microfluidic chip of the invention, comprises a flow. This is so, according to the invention, whether or not the sperms are carried by a stream of fluid also comprising a flow, or whether the sperms are caused to move by some other direct or indirect force or motivation, and whether or not the nature of any motivating force is known or understood. The application of any force may be used to provide a flow, including without limitation, pressure, capillary action and combinations thereof, without regard for any particular theory or mechanism of action, so long as sperms are directed for detection, measurement, sorting or activating according to the invention.

The term "motility" refers to the capability of movement, and "sperm motility" specifically to those properties of a sperm cell that allows movement through a fluid medium.

The term "active sperm" refers to those sperm cells which are both motile and moving progressively.

The term "flow channel" is a channel of the chip of the invention which permits the flow of sperms into a region for sorting and/or activating. The flow channel is typically in fluid communication with an open region receiving a sperm sample, which permits the flow of sperms into the flow channel. The flow channel is also typically in fluid communication with the region for sorting and/or activating.

The term "inlet region" is an area of a microfluidic chip that receives sperms. The inlet region may contain an inlet channel, a well or reservoir, an opening, and other features which facilitate the entry of sperms into the chip. The inlet region is in fluid communication with the flow channel and is upstream therefrom. A chip may contain more than one inlet region if desired. The term "outlet region" is an area of a microfluidic chip that collects or dispenses sperms after sorting. An outlet region is downstream from a flow channel, and may contain a reservoir, branch channels or outlet channels. A chip may contain more than one outlet region if desired.

The term "sperm" refers to sperm cells from any animal such as human, pig, horse, dog, sheep, cattle, goat, cat and so on. The sperm cell consists of a head, a midpiece and a tail. The head contains the nucleus with densely coiled chromatin fibres, surrounded anteriorly by an acrosome, which contains enzymes used for penetrating the female egg. The term "sperm sample" refers to semen or diluted semen.

The term "subgroup" and "subpopulation" are used interchangeable. The subgroup or subpopulation of sperms includes the following Group (0), Group (1), Group (2) and Group (3). Group 0 (G0):
This subpopulation showed the lowest values of VCL (VCL=0 μm/sec). Subpopulation 1 was defined by overall low values of velocity, based on the results of VCL, VSL and VAP, low values of linearity, as indicated by values of LIN and STR, and low values of oscillatory movement, as indicated by WOB, mean ALH and BCF values.
Group 1 (G1):
This subpopulation was characterized by the second lowest values of VCL (VCL=0-120 μm/sec). Sperm included in Subpopulation 2 showed middle-to-high velocity, as indicated by VCL, VSL and VAP, high linearity, as indicated by LIN and STR, and high values of oscillatory movement, as indicated by WOB, mean ALH and BCF values.
Group 2 (G2):
This subpopulation had high values of VCL (VCL=120-180 μm/sec). Subpopulation 3 was made up of sperm with high velocity and relatively high linearity, as indicated by VCL, VSL, VAP, LIN and STR. Moreover, sperm included in this subpopulation also had a relatively high oscillatory movement, as indicated by values of WOB, mean ALH and BCF values.
Group 3 (G3):
This subpopulation included that sperm with the highest VCL (VCL>180 μm/sec). Subpopulation 4 was made up of sperm with highest velocity and linearity characteristics, as indicated by values of VCL, VSL, VAP, LIN and STR. Furthermore, the overall oscillatory movement of these spermatozoa was also very high, as indicated by WOB, mean ALH and BCF values.

Microfluidic Chip of the Invention

The microfluidic chip of the invention can acquire sperms with high motility and/or activity by constructing a divergent structure and an optional block structure with rounded corners. First, the invention designs a microfluidic chip with a divergent structure and this divergent structure can group sperms according to their velocity. Furthermore, the invention designs a block structure with rounded corner to activate the sperms so that the numbers of the sperms with higher velocity and activity are increased.

In one aspect, the invention provides a microfluidic chip for acquiring sperms with high motility in a sperm sample, which comprises:

(a) an inlet region at one end of the microfluidic chip;
(b) a first flow channel that is in fluidic communication with the inlet region;
(c) a divergent channel, which is arranged at the downstream of the flow channel and in fluidic communication with the flow channel; and
(d) one or more outlet region(s) located at one or both sides of the divergent channel.

A microfluidic chip according to the invention comprises an inlet region, a flow channel, a divergent channel, and one or more outlet region(s) located at one or both sides of the divergent channel.

Referring the drawings, FIG. 1 is an overall view of the microfluidic chip of the invention. The inlet region 11 introduces a sperm sample into the flow channel 12. Preferably, the inlet region is in circle shape and has a diameter ranging from about 0.5 mm to about 4 mm. More preferably, the diameter of the inlet region is about 1 mm. Preferably, the sperm sample can be fed to the inlet region by injecting it thereinto.

The flow channel 12 of the microfluidic chip is in fluidic communication with the inlet region 11. Preferably, the length of the flow channel ranges from about 5 mm to about 30 mm, or about 6 mm to about 30 mm, about 7 mm to about 30 mm, about 8 mm to about 30 mm, about 9 mm to about 30 mm, about 10 mm to about 30 mm, about 11 mm to about 30 mm, about 12 mm to about 30 mm, about 13 mm to about 30 mm, about 15 mm to about 30 mm, about 16 mm to about 30 mm, about 17 mm to about 30 mm, about 18 mm to about 30 mm, about 19 mm to about 30 mm or about 20 mm to about 30 mm; more preferably, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm or about 30 mm; more preferably, about 25 mm. Preferably, the width of the flow channel ranges from about 50 μm to about 150 μm, about 60 μm to about 150 μm, about 70 μm to about 150 μm, about 80 μm to about 150 μm, about 90 μm to about 150 μm, about 100 μm to about 150 μm, about 50 μm to about 140 μm, about 50 μm to about 130 μm, about 50 μm to about 120 μm, about 50 μm to about 110 μm, about 50 μm to about 100 μm, about 60 μm to about 140 μm, about 60 μm to about 130 μm, about 60 μm to about 120 μm, about 70 μm to about 140 μm, about 70 μm to about 130 μm, about 70 μm to about 120 μm, about 80 μm to about 140 μm, about 80 μm to about 130 μm, about 80 μm to about 120 μm, about 80 μm to about 110 μm, about 90 μm to about 130 μm, about 90 μm to about 120 μm or about 90 μm to about 110 μm; more preferably, about 90 μm, about 91 μm, about 92 μm, about 93 μm, about 95 μm, about 96 μm, about 97 μm, about 98 μm, about 99 μm, about 100 μm, about 101 μm, about 102 μm, about 103 μm, about 104 μm, about 105 μm, about 106 μm, about 107 μm, about 108 μm, about 109 μm or about 110 μm. Preferably, the depth of the flow channel ranges from about 25 μm to about 75 μm, about 25 μm to about 70 μm, about 25 μm to about 65 μm, about 25 μm to about 60 μm, about 25 μm to about 55 μm, about 25 μm to about 50 μm, about 25 μm to about 70 μm, about 25 μm to about 65 μm, about 25 μm to about 60 μm, about 25 μm to about 55 μm, about 25 μm to about 50 μm, about 30 μm to about 70 μm, about 30 μm to about 65 μm, about 30 μm to about 60 μm, about 30 μm to about 55 μm, about 35 μm to about 70 μm, about 35 μm to about 65 μm, about 35 μm to about 60 μm, about 35 μm to about 55 μm, about 40 μm to about 60 μm, about 40 μm to about 55 μm, or about 45 μm to about 55 μm; more preferably, about 45 μm, about 46 μm, about 47 μm, about 48 μm, about 49 μm, about 50 μm, about 51 μm, about 52 μm, about 53 μm, about 54 μm or about 55 μm.

The divergent channel 13 is arranged at the downstream of and is in fluidic communication with the flow channel 12. The end of the divergent channel is open. The width of the divergent channel is gradually enlarged starting from that of the flow channel 2. In one embodiment, the width of the divergent channel 3 increases by more than 1 time to 15 times of that of the flow channel 2; preferably, more than 1 time to 14 times, more than 1 time to 13 times, more than 1 times to 12 times, more than 1 time to 11 times, more than 1 time to 10 times, more than 1 time to 9 times, more than 1 time to 8 times, more than 1 time to 7 times, more than 1 time to 6 times, more than 1 time to 5 times, more than 1 time to 4 times, more than 1 time to 3 times or more than 1 times to 2 times; more preferably, more than 1 time to 10 times. Preferably, the width of the divergent channel 3 ranges from about 50 μm to about 1,000 μm, about 60 μm to about 1,000 μm, about 70 μm to about 1,000 μm, about 80 μm to about 1,000 μm, about 90 μm to about 1,000 μm, about 100 μm to about 1,000 μm, about 100 μm to about 900 μm, about 100 μm to about 800 μm or about 100 μm to about 700 μm. In another embodiment, the angle between the wall of the divergent channel and the wall of the flow channel is about 5 to about 30 degrees; preferably, the angle is about 5 to about 25 degrees, about 5 to about 20 degrees, about 5 to about 15 degrees or about 5 to about 12 degrees; more preferably, the angle is about 8 to about 20 degrees, about 8 to 15 degrees, about 8 to 12 degrees; most preferably, the angle is about 10 degrees. In another embodiment, the flow velocity V is determined mainly with the flow volume of the sperm sample Q and the cross sectional area of the divergent channel A. Preferably, the flow velocity is determined according to a formula of $V=Q/A$, wherein V is velocity, Q is flow volume of the sperm sample and A is the cross sectional area of the divergent channel. More preferably, the ratio of the cross sectional area to the flow velocity is from about 1 to about 1/10. The sperm sample flows from the flow channel 2 to the divergent channel 3. Since the divergent channel has larger cross-sectional dimensions than those of the flow channel, the flow rate of the middle stream of the sperm sample is higher than that of the side stream of the sperm sample in the divergent channel. In view of the fact that sperms have a property of swimming counter-current, the sperms having higher motility are capable of resisting the flow resistance of the stream. Accordingly, the divergent channel 13 comprises one or more outlet region(s) 14 located at one or both sides of the divergent channel 13 to grade sperms with various motility scales.

In one embodiment, the invention provides a microfluidic chip for acquiring sperms with high motility in a sperm sample, which comprises:

(a) an inlet region at one end of the microfluidic chip;
(b) a first flow channel that is in fluidic communication with the open region of (a);
(c) a divergent channel, which is arranged at the downstream of the flow channel and in fluidic communication with the flow channel;
(d) one or more outlet region(s) located at one or both sides of the divergent channel;
(e) a second flow channel arranged at the downstream of the divergent channel; and
(f) an outlet region at the opposite end of the inlet region of (a) of the microfluidic chip and in fluidic communication with the second flow channel.

In one embodiment, the above microfluidic chip further comprises a block structure with rounded corners located at the divergent channel or the second flow channel, wherein a distance is kept between each side of the block structure and the wall of the channel.

Figure 2A:
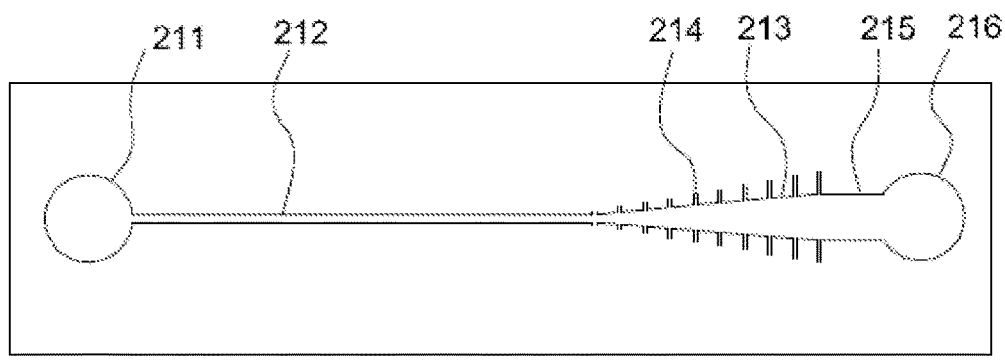
FIG. 2A shows an overall view of the microfluidic chip of the invention comprising an inlet region, first flow channel, a divergent channel, a second flow channel and an outlet region.
Figure 2B:
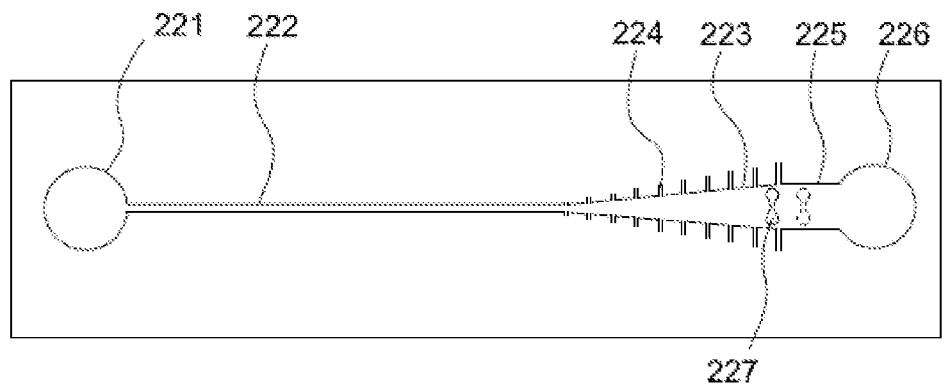
FIG. 2B shows an overall view of the microfluidic chip of the invention comprising an inlet region, first flow channel, a divergent channel, a second flow channel, a block structure with rounded corners and an outlet region.

Referring to FIG. 2A in addition to inlet region 211, flow channel 212, divergent channel 213 and outlet region(s) 214 as mentioned in the above FIG. 1, a second flow channel 215 and an outlet region 216 are provided. Referring to FIG. 2B, in addition to inlet region 221, flow channel 222, divergent channel 223 and outlet region(s) 224 as mentioned in the above FIG. 1, a second flow channel 225, a block structure 227 with rounded corners and an outlet region 226 are provided.

Referring to FIG. 2A and FIG. 2B, subsequent to the divergent channel 213 (FIG. 2A) or 223 (FIG. 2B), a second flow channel 215 (FIG. 2A) or 225 (FIG. 2B) is provided. The second channel is arranged at the downstream of the divergent channel 3 and is in fluidic communication with the divergent channel. Preferably, the length of the flow channel ranges from about 0.5 mm to about 3 mm, or about 0.5 mm to about 2 mm or about 0.5 mm to about 1 mm.

Figure 2C:
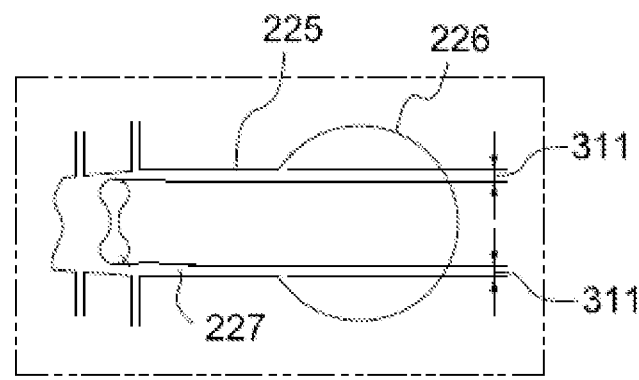
FIG. 2C shows the enlarged plot of the block structure.

In the embodiment shown in FIG. 2B, there is a block structure 227 with rounded corners located in the divergent channel 223 or a second flow channel 225. According to the invention, the block structure with rounded corners may be dumb-bell structure with rounded corners, a cylinder structure with rounded corners, a cuboid structure with rounded corners, a cube structure with rounded corners or trapezoid bulk structure with rounded corners. Preferably, the block structure with rounded corners is a dumb-bell structure with rounded corners. Preferably, the block structure 227 with rounded corners locates at the end of the divergent channel. According to the invention, as shown in FIG. 2C, there is a distance 311 between each side of the block structure with rounded corners and the wall 225 of the divergent channel. Preferably, the distance ranges from about 100 µm to about 10 µm; more preferably, about 90 µm to about 10 µm, about 80 µm to about 10 µm, about 70 µm to about 10 µm, about 60 µm to about 10 µm, about 50 µm to about 10 µm, about 40 µm to about 10 µm or about 30 µm to about 10 µm, about 100 µm to about 20 µm, about 90 µm to about 20 µm, about 80 µm to about 20 µm, about 70 µm to about 20 µm, about 100 µm to about 30 µm, about 90 µm to about 30 µm, about 80 µm to about 30 µm, about 80 µm to about 40 µm, about 80 µm to about 50 µm, about 75 µm to about 30 µm, about 75 µm to about 40 µm, about 75 µm to about 50 µm, about 75 µm to about 60 µm; further more preferably, about 59 µm, about 58 µm, about 57 µm, about 56 µm, about 55 µm, about 54 µm, about 53 µm, about 52 µm, about 51 µm or about 50 µm. According to the invention, the flow velocity at the narrowest location within the block structure is determined according to (Q/2) and maximum width of the divergent channel. In one embodiment, the flow velocity is determined according to a formula of V=(Q/2)/(maximum width (µm) of the divergent channel/S), wherein V is velocity, Q is flow volume of the sperm sample and S is the distance between each side of the block structure and the wall of the channel.

As mentioned above, the flow velocity at the middle of the flow stream is higher than that of the flow stream near the channel wall at both sides in the divergent channel 3. In view of the fact that sperms have a property of swimming counter-current, the sperms having higher motility are capable of resisting higher flow resistance of the stream and being collected to locations with narrower channel width. Accordingly, the divergent channel 3 comprises one or more outlet region(s) 4 located at one or both sides of the divergent channel 3 to collect sperms with high motility. The sperms in the middle stream in the divergent channel 3 will continue to flow through the block structure with rounded corners 31. As shown in FIG. 2C, the block structure with rounded corners 227 provides an obstacle to the sperm stream so that the sperms flow through the space between each side 311 of the block structure with rounded corners and the wall 225 of the divergent channel and the flow velocity thereof dramatically increases. By largely increasing the flow velocity of the sperm stream, the sperms will be activated by sperm capacitation, so more amounts of motile sperms can be obtained.

At the end of the microfluidic chip of the invention, an outlet region 216 (FIG. 2A) or 226 (FIG. 2B) is provided to collect sperms with high motility and is in fluidic communication with the second flow channel 215 (FIG. 2A) or 225 (FIG. 2B). Preferably, the outlet region is in circle shape and has a diameter ranging from about 0.5 mm to about 4 mm. More preferably, the diameter of the outlet region is about 1 mm.

Figure 3A:
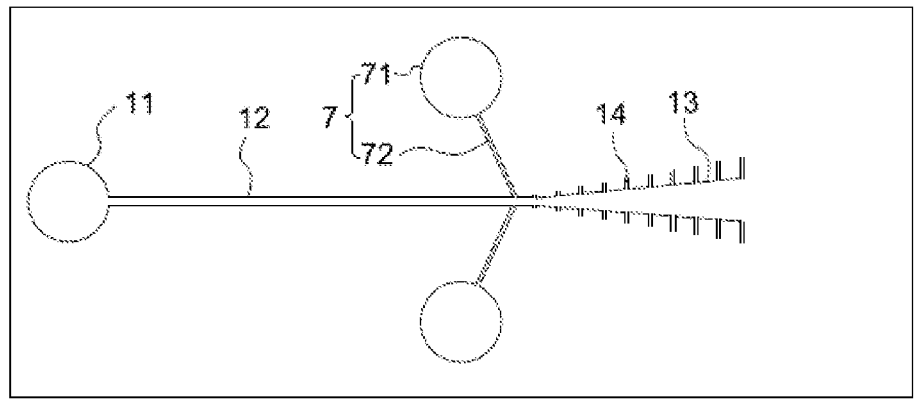
FIG. 3A shows an overall view of the microfluidic chip of the invention comprising in addition to those shown in FIG. 1, a squeeze flow channel with inlet region arranged prior to the divergent channel.
Figure 3B:
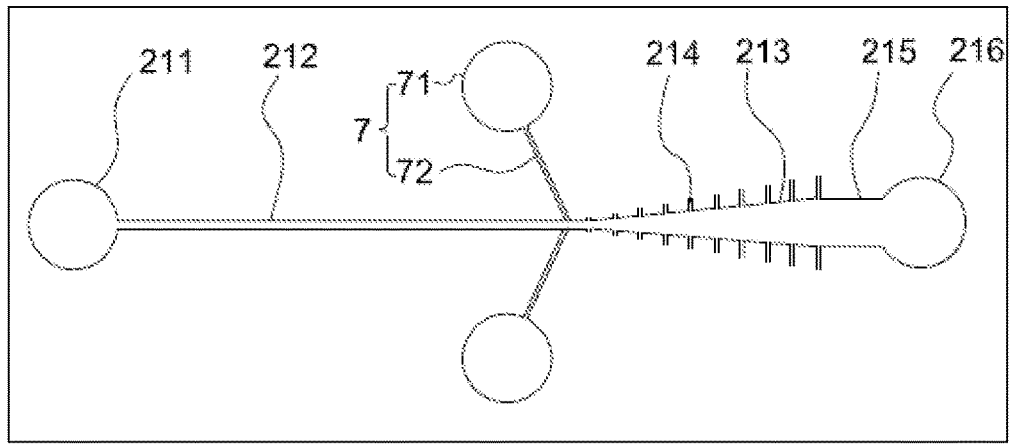
FIGS. 3B and 3C show an overall view of the microfluidic chip of the invention comprising in addition to those shown in FIG. 2A and FIG. 2B, respectively, a squeeze flow channel with inlet region arranged prior to the divergent channel.
Figure 3C:
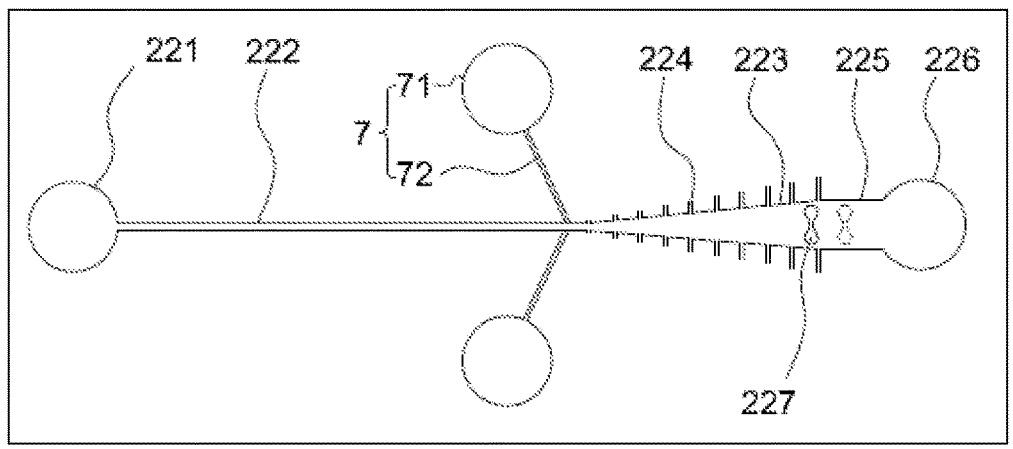

In another embodiment, referring to FIG. 3A, one or two squeeze flow channel(s) 7 with inlet region is (are) arranged prior to the divergent channel 14 of the microfluidic channel as shown in FIG. 1 to provide a medium squeeze flow to the sperm sample stream. The embodiments of the microfluidic chips shown in FIG. 2A and FIG. 2B can have the above-mentioned additional squeeze flow channel(s), as shown in FIG. 3B and FIG. 3C. Joint location of squeeze flow channel(s) and flow channel can be anywhere between inlet and divergent channel. The chip is designed to control fluid direction and speed by pinching force and generate stable and slow flow speed. The flow distribution in converge point is controlled by the liquid height of branching flow channel, concentrating sperms according to their motility. Another purpose of this design is for drug administration at branching inlet, such as progesterone, and mix in central flow channel. Each squeeze flow channel 7 comprises a flow channel 72 and an open region 71. The angle between the wall of the squeeze flow channel and the first flow channel ranges from about 30 degrees to about 120 degrees. Preferably, the angle is about 30 degrees, 45 degrees, about 90 degrees or about 120 degrees. When the angle is from about 30 degrees to 90 degrees, the medium squeeze flow is co-current with the sperm sample stream. When the angle is from 90 degrees to 120 degrees, the medium squeeze flow is counter-current with the sperm sample stream. By providing squeeze flow into the sperm sample stream, the sperms with high motility can be increased in the divergent channel.

In another embodiment, after sperms are collected from the open region, a buffer can be added into outlet region of the microfluidic chips shown in FIG. 2A, FIG. 2B, FIG. 3A, FIG. 3B or FIG. 3C to flush back sperms within flow channel and collect from the inlet region. After loading of sperm sample into inlet region, flow channel is formed by hydrostatic pressure and capillary action. Due to the property of swimming counter-current of sperms, the subgroup with higher mobility will retain in the flow channel and the one with slower mobility will be pushed, along with dead sperms and waste toward the outlet region. When flow channel becomes equilibrium, atmospheric pressure is insulated by the cover of inlet region. After withdrawing the waster from the outlet region, buffer is added into the outlet to flush back sperms within the flow channel and collect from the inlet region.

Figure 4:
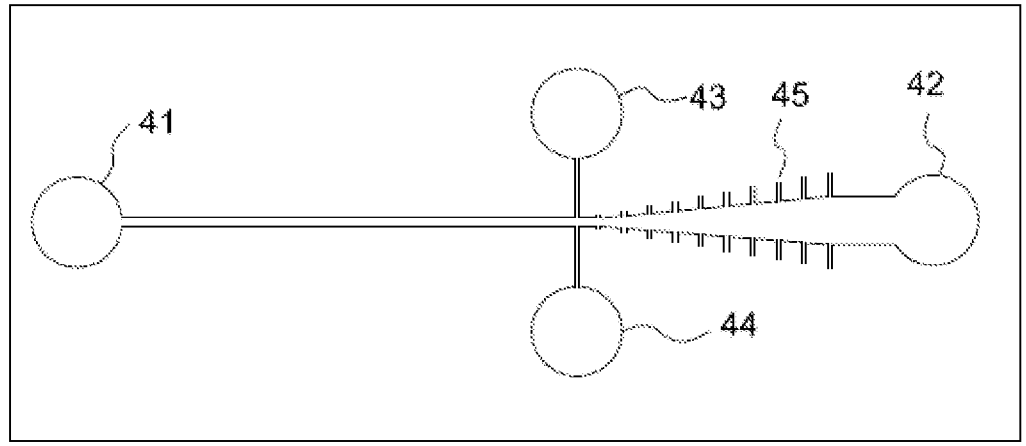
FIG. 4 shows an overall view of the microfluidic chip of the invention with additional outlets arranged prior to the divergent channel.
Figure 5:
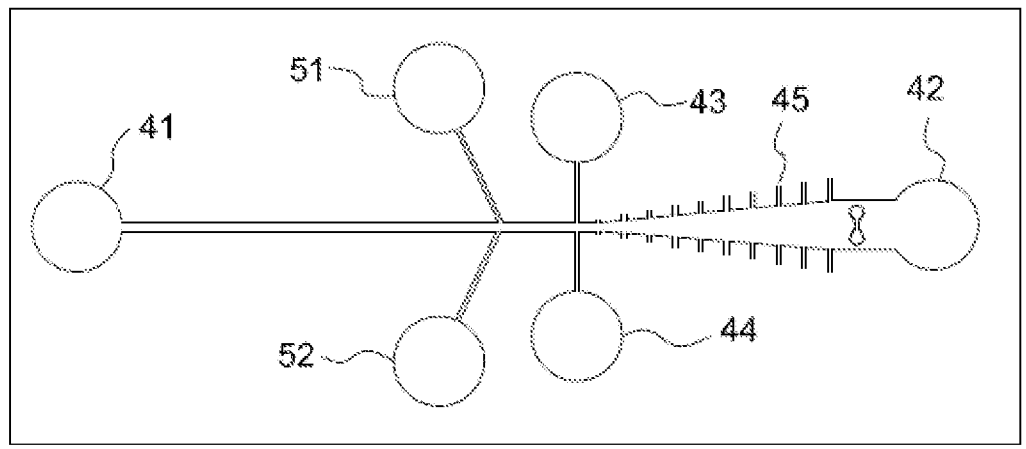
FIG. 5 shows an overall view of the microfluidic chip of the invention possible port arrangements prior to the divergent channel but after the squish channel(s).

In another embodiment, in addition to the outlet region 42 at the opposite end of the open region 41, one or two additional outlets 43 and 44 can be arranged prior to the divergent channel 45, as shown in FIG. 4. For the microfluidic chip having one or two squeeze flow channel(s) 51 and 52, the outlets 43 and 44 can be arranged prior to the divergent channel 45 but after the squeeze flow channel(s) 51 and 52, as shown in FIG. 5. Preferably, the angle between the wall of the outlet(s) and the first flow channel is about less than 90 degrees; preferably, about 90 degrees. In one embodiment, the chip is also can be used to reverse flush high motile sperms into the outlet(s) of vertical branche(s), avoiding the interference of original semen after backflushing. Referring to FIG. 4, after insulation of outlet 43 and outlet 44, semen is loaded into inlet region 41. Flow stream in flow channel is formed by hydrostatic pressure and capillary action. Due to the property of swimming counter-current of sperms, the subgroup with high mobility sperms will retain in the flow channel and the dead sperms and waste will appear in the outlet region 42. When flow channel becomes equilibrium, flow channel stay static. After withdrawing the waster from outlet region 42, buffer is added into outlet region 42 to flush back sperms within flow channel and collect from outlets 43 and 44. Referring to FIG. 5, semen is loaded into inlet region 41 and buffer or drug is loaded into squeeze flow channels 51 and 52. Flow channel is formed by hydrostatic pressure and pinching force. Due to the property of swimming counter-current of sperms, the subgroup with high mobility sperms will retain in the flow channel and the dead sperms and waste will appear in the outlet region. When flow channel becomes equilibrium, atmospheric pressure is insulated by the cover of inlet 41, 51, and 52. After withdrawing the waster from outlet region 42, buffer is added into outlet region 42 to flush back sperms within flow channel and collect from squeeze flow channels 51 and 52.

Figure 6:
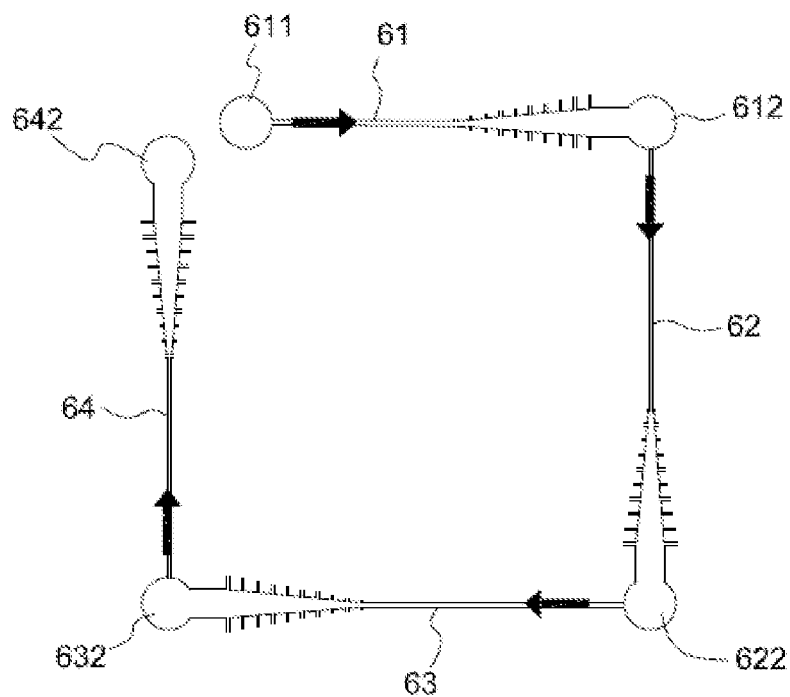
FIG. 6 shows a sequential operation assembly of the microfluidic chips of the invention.

In another aspect, the invention provides a sequential operation assembly of the microfluidic chips, comprising more than one chips of the invention, wherein the chips are arranged in sequential. Sequential operation of collecting sperms is designed. Before flow equilibrium establishes, some high motile sperms will be flushed into outlet. In one embodiment, to preserve all high quality sperms, the chip also can be used to sort sperms by four sequential microfluidic channels to reduce the loss of high quality sperms. Referring to FIG. 6, after loading of semen into inlet region 611, flow channel is formed by hydrostatic pressure and capillary action. Due to the property of swimming counter-current of sperms, the subgroup with high mobility sperms will retain in the flow channel and the dead sperms and waste will appear in the outlet region 612. Sample in outlet region 612 will be sorted by the second 62, third 63, and fourth 64 microfluidic channels. When flow channel becomes equilibrium, flow channel stay static. We can collect sample from inlet region 611, outlet region 612, outlet region 622, or outlet region 632 according to the demand of sperm numbers. Depends on collected sperm number from inlet region 611, sorting sperms from outlet regions 612, 622, and 632 will be considered to preserve.

Figure 7:
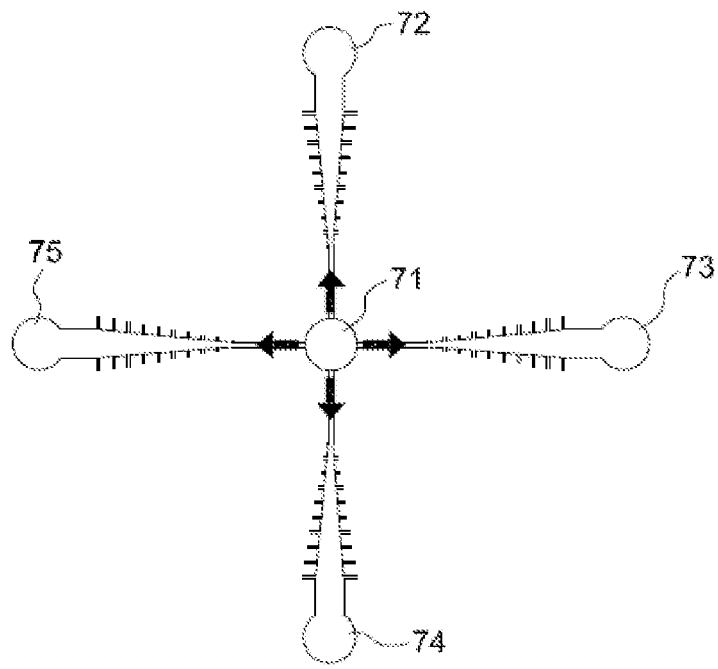
FIG. 7 shows a parallel operation assembly of the microfluidic chips of the invention.

In another aspect, the invention provides a parallel operation assembly of the microfluidic chips, comprising more than one chips of the invention, wherein the chips are arranged in parallel. Parallel operation of collecting sperms is designed. The chip is designed as the combination of four microfluidic channel into one chip. When specimens are overloading, we can increase sorting yields to 4-fold by operating four microfluidic channel at the same time. Referring to FIG. 7, after loading of semen into central inlet region 71, flow channel is formed by hydrostatic pressure and capillary action. Due to the property of swimming counter-current of sperms, the subgroup of high mobility will retain in the flow channel and the dead sperms and waste will appear in four outlet regions 72, 73, 74 and 75. In one embodiment, when flow channel becomes equilibrium, atmospheric pressure is insulated by the cover of inlet. After withdrawing the waster from outlets, buffer is added into outlet regions 72, 73, 74 and/or 75 to flush back sperms within flow channel and collect from inlet region 71.

Figure 8:
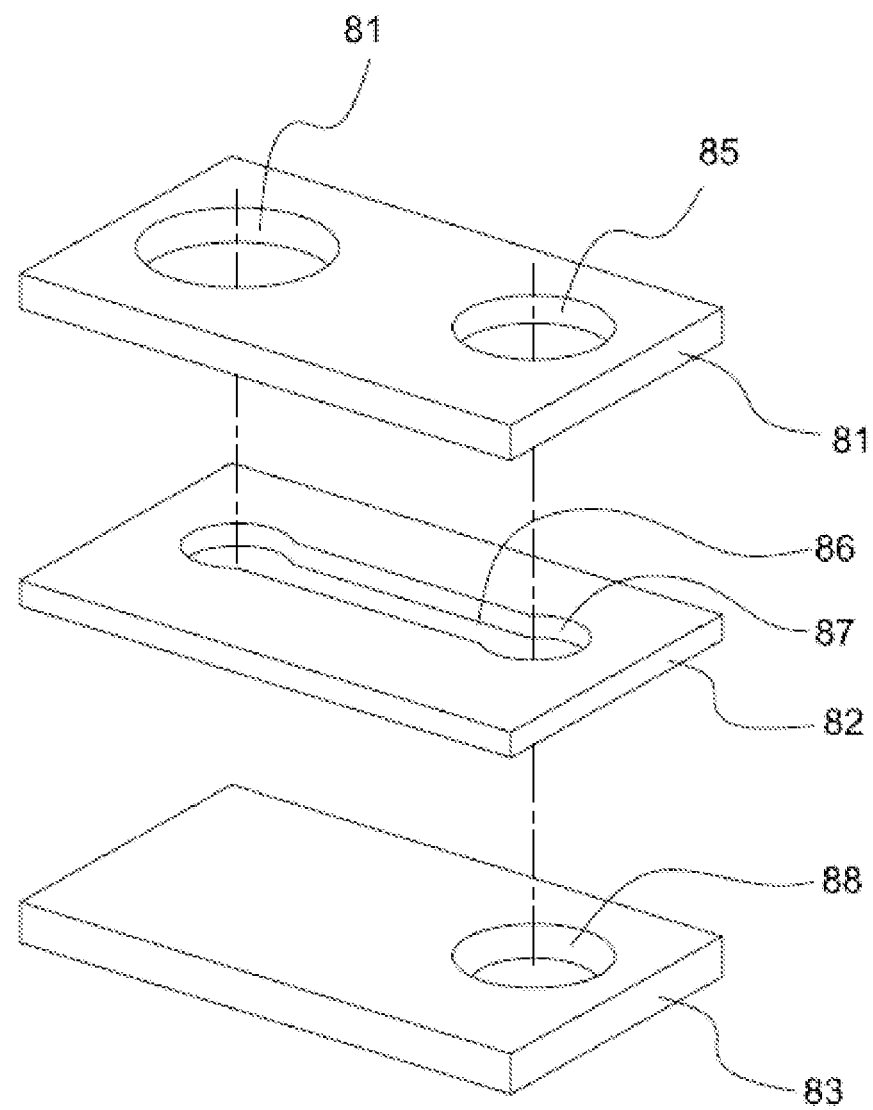
FIG. 8 shows a high throughput sperm sorting.

In a further aspect, a high throughput sperm sorting device is designed. The high throughput sperm sorting device comprises a first layer, a second layer and a third layer, wherein the first layer locates on the top of the device and has an inlet region at one end of the microfluidic chip and an outlet region at the opposite end of the open region of (a) of the microfluidic chip, the second layer locates between the first layer and the third layer and has a microfluidic chip of the invention and the inlet region of the chip connects with the inlet region at the first layer, and the third layer locates at the bottom of the device and has a reservoir that connects the outlet region of the chip at the second layer. Referring to FIG. 8, the chip is divided into three layers 81, 82 and 83: the first layer 81 contains two opens as inlet region 84 and outlet region 85; the second layer 82 is designed for microfluidic channel 86 and the outlet region 87 is connected to the third layer 83; the third layer 83 has waster reservoir 88 responsible for collecting waster from outlet and maintaining hydrostatic pressure within flow channel. In one embodiment, after loading of semen into inlet region 84, flow channel is formed by hydrostatic pressure and capillary action, which subgroup motile sperms due to their adverse swimming character, and dead sperms and waste will appear in outlet region 87. When flow channel becomes equilibrium, atmospheric pressure is insulated by the cover of inlet region 84. After withdrawing the waster from outlet region 87, buffer is added into outlet region 87 to flush back sperms within flow channel and collect from inlet region 84.

Production of Microfluidic Chip of the Invention

The microfluidic chip channels of the invention are microfabricated, for example by etching a silicon chip using conventional photolithography techniques, or using a micromachining technology called "soft lithography". These and other microfabrication methods may be used to provide inexpensive miniaturized devices, and in the case of soft lithography, can provide robust devices having beneficial properties such as improved flexibility, stability, and mechanical strength. Devices according to the invention are relatively inexpensive and easy to set up. They can also be disposable. Using these kinds of techniques, microfabricated fluidic devices can replace the conventional fluidic flow chambers of the prior art.

A microfabricated device of the invention is preferably fabricated from a silicon microchip or silicon elastomer. It shall be appreciated that the "regions" and "channels" are in fluid communication with each other and therefore may overlap; i.e., there may be no clear boundary where a region or channel begins or ends. A microfabricated device can be transparent and can be covered with a material having transparent properties.

In a preferred embodiment, the invention provides channels molded into optically transparent silicone rubber, poly (methyl methacrylate) (PMMA), poly(lactic acid), polylactide (PLA) or PolyDiMethylSiloxane (PDMS), preferably PDMS. PDMS process has been reported by Samuel K. Sia and George M. Whitesides (Electrophoresis 2003, 24, pp. 3563-3576). This is cast from a mold made by etching the negative image of these channels into the same type of crystalline silicon wafer used in semiconductor fabrication. As described above, the same techniques for patterning semiconductor features are used to form the pattern of the channels. The uncured liquid silicone rubber is poured onto these molds placed in the bottom of a slide. To speed the curing, these poured molds are baked. After the PDMS has cured, it is removed from on top of the mold and trimmed. Before use, the PDMS device is placed in a hot bath of HCl to make the surface hydrophilic. The device is then placed onto a No. 1 (150 µm thick) (25×25 mm) square microscope cover slip. The cover slip forms the floor (or the roof) for all channels and wells. Note that any of or all of these manufacturing and preparation steps can be done by hand, or they can be automated, as can the operation and use of the device.

Kits and Methods for Acquiring Sperms with High Motility by Using the Microfluidic Chip of the Invention In another aspect, the invention provides a method for acquiring sperms with high motility, comprising optionally mixing a sperm sample with an activating agent and applying the resulting sperm sample to the microfludic chip of the invention. According to the invention, the activating agent is pentoxifylline, xanthine, xanthine oxidase, albumin or progesterone. Accordingly, the invention provides a kit for acquiring sperms with high motility, comprising an activating agent and a microfludic chip of the invention.

System for Acquiring Sperms with High Motility

In a further embodiment, the invention provides a system for acquiring sperms with high motility, comprising a microfluidic chip of the invention, an optional activating agent, a microfluidic dispensing system and a sensor for detecting sperm quality. Any microfluidic dispensing system and sensor known in the art can be combined with the microfluidic chip of the invention to provide a system for acquiring sperms with high motility.

The microfluidic chip can achieve the process of acquiring sperms in one step and the difference in sperm motility or concentration between raw semen samples can be ignored before the process using the chip of the invention. The microfluidic chip of the invention can screen subpopulations of motile sperms and obtain higher amounts of motile sperms. In addition, the microfluidic chip is disposable, easy to produce and low cost, so it is advantageous product in acquiring motile sperms.

EXAMPLE

Example 1 Preparation of Microfluidic Chip of the Invention

The microfluidic chip having microscale flow channels, valves and other elements can be designed and fabricated from a solid substrate material. Silicon is a preferred substrate material due to well-developed technology permitting its precise and efficient fabrication, but other materials may be used, including polymers such as polytetrafluoroethylenes. Micromachining methods well known in the art include film deposition processes, such as spin coating and chemical vapor deposition, laser fabrication or photolithographic techniques, or etching methods, which may be performed by either wet chemical or plasma processes.

The initial steps in microfabricating the microfluidic chip of the invention involve SU-8 thick resist processes. A glass substrate was washed using standard washing procedures with acetone, isopropanol and distilled water and then spun dry. A layer SU8-50 photoresist, preferably about 50 µm in thickness, was formed on the glass substrate, typically by heating the glass substrate to 800 to 1200° C. The coated laminate is irradiated through a photomask which has been imprinted with a pattern corresponding in size and layout to the desired pattern of the microfluidic channels. Methods for forming photomasks having desired photomask patterns are well known.

Microfluidic sperm-acquiring channels were made using soft lithographic methods. Briefly, PDMS was cast onto a master mold with the desired channel features and cured. Resulting PDMS stamps were oxidized to seal channels onto a glass cover slide to obtain the microfluidic chip of the invention. Various types of microfluidic chips of the invention are shown in FIGS. 1 to 8.

Example 2 Assays for Acquiring and Analysis of Motile Sperms

Acquiring of Human Sperms Using Microfluidic Chip of the Invention

The human sperms are classified as the following three grades according to their curvilinear velocity (VCL).

Group 0 (G0): VCL being 0 µm/s (sperm is live but VCL being neglectable);
Group 1 (G1): VCL<120 µm/s;
Group 2 (G2): VCL being 120-180 µm/s;
Group 3 (G3): VCL>180 µm/s.

Semen sample with high concentration ($60 \times 10^6$ sperms/ml) was obtained from humans. Each sample was treated and measured as follows. 1 ml PureSperm80 (Sepal Reproductive Devices, MA, U.S.A.), 1 ml PureSperm 40 (Sepal Reproductive Devices, MA, U.S.A.) and 1.5 ml of the sample were added to 15 ml microcentrifuge tube and then centrifuged at 25° C., 300 rcf (relative centrifugal force) for 30 minutes. After centrifugation, the supernatant was removed and then 5 ml of PureSperm Wash for washing. The resulting solution was centrifuged at 25° C., 500 rcf for 20 minutes. After centrifugation, the supernatant was removed to obtain pellet. The pellet was solved with 500 µl Biggers-Whitten-Whittingham (BWW) medium. Then, the concentration of sperms was adjusted to $20\text{-}25 \times 10^6$ sperm/ml.

Sperm acquiring assays were then preformed. 10 ml of phosphate buffer was injected to the microfluidic chip of the invention so that there was no bubble in the channels of the chip. The sperm samples were introduced into the inlet region of the microfluidic chip of the invention. In the divergent channel, the velocity can be obtained by velocity (V)=flow (Q)/cross sectional area of the divergent channel (A). In the example, Q is 0.8 m/s and the angle between the wall of the divergent channel and the stream flow direction in the flow channel is 10 degrees, so the flow velocities at different positions of the divergent channel are shown in the table below:

| Position(μm) | 100 | 200 | 300 | 400 | 500 | 600 | 700 | 800 | 900 | 1000 |
|---|---|---|---|---|---|---|---|---|---|---|
| Flow velocity (μm/s) | 163 | 81.5 | 54.33 | 40.75 | 32.6 | 27.17 | 23.29 | 20.38 | 18.11 | 16.3 |

The sample solution was aspirated from the outlet region of the chip of the invention. The resulting sample was measured by medeaLAB CASA (MedComputer Aided Sperm Analyzer; Medical Technology Vertriebs-GmbH, Germany).

For the sperm sample with the concentration of $60 \times 10^6$ sperms/ml, the numbers of the sperms in various VCL groups before and after treatment are listed in below table:

| Group | Numbers of Sperms Before Treatment with Chip (10 μl) | Numbers of Sperms After Treatment with Chip (6 μl) |
|---|---|---|
| G 0 | 88,247 (15%) | 46,887 (20%) |
| G 1 | 49,174 (8%) | 20,489 (9%) |
| G 2 | 139,898 (23%) | 16,868 (7%) |
| G 3 | 322,681 (54%) | 153,240 (65%) |
| Total | 600,000 (100%) | 237,484 (100%) |

Figure 9:
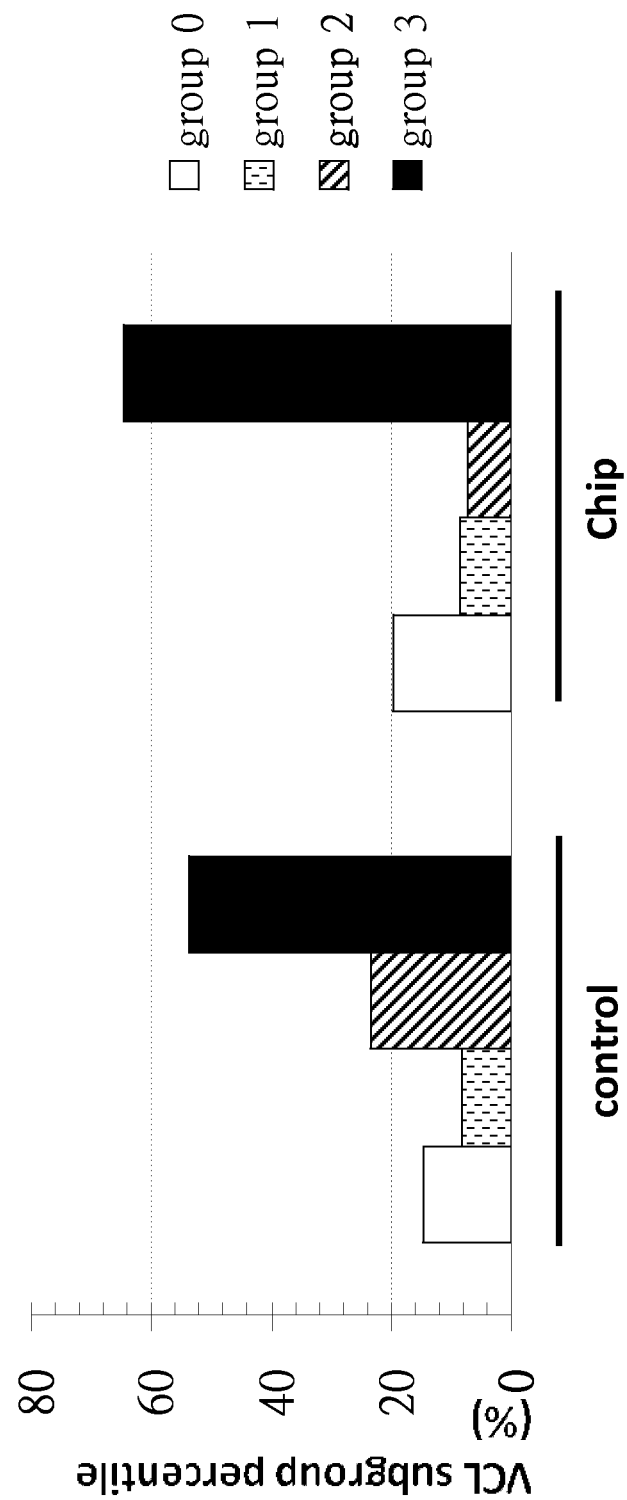
FIG. 9 shows the acquiring results of the semen sample with concentration of $60 \times 10^6$ sperms/ml.

The results in the above table are shown in FIG. 9. After treatment of the sperm sample with the chip of the invention, the G3 group of sperms increases from 54% to 65% and the G2 group of sperms reduces from 23% to 7%.

Figure 10:
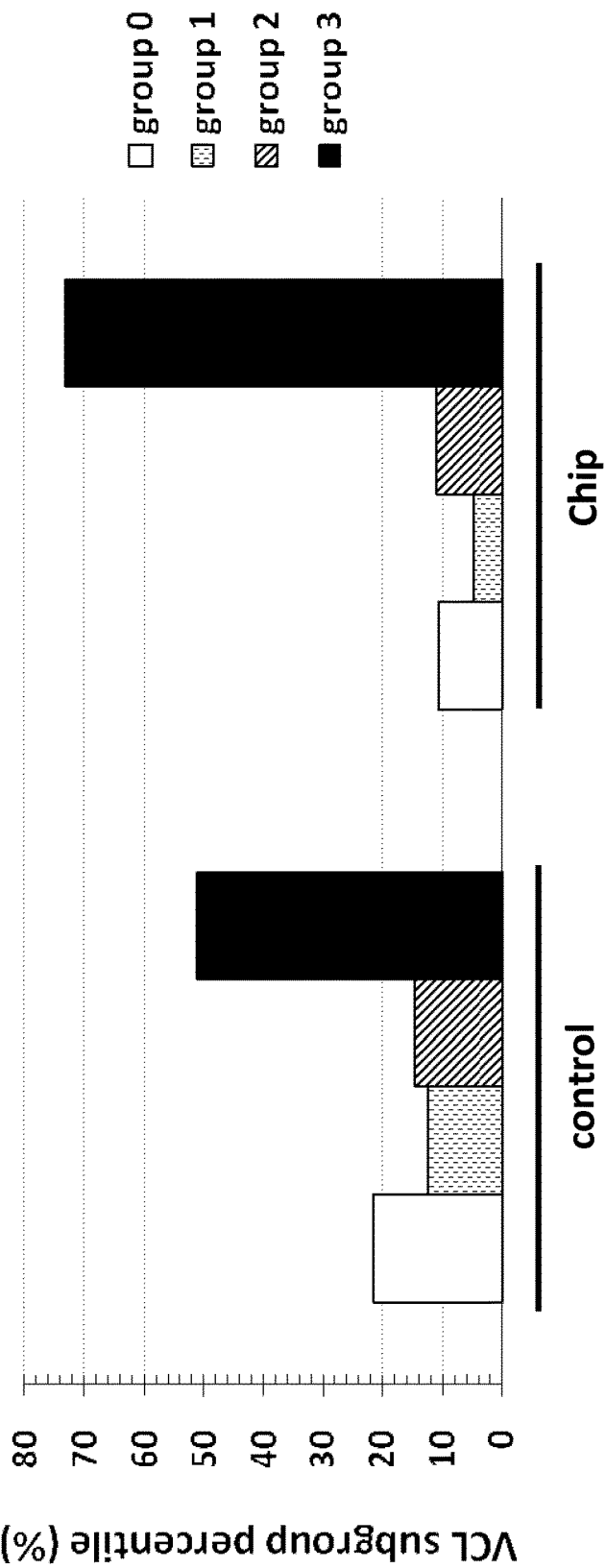
FIG. 10 shows the acquiring results of the human semen sample with concentration of $60 \times 10^6$ sperms/ml, using the microfluidic chip of the invention.
Figure 11:
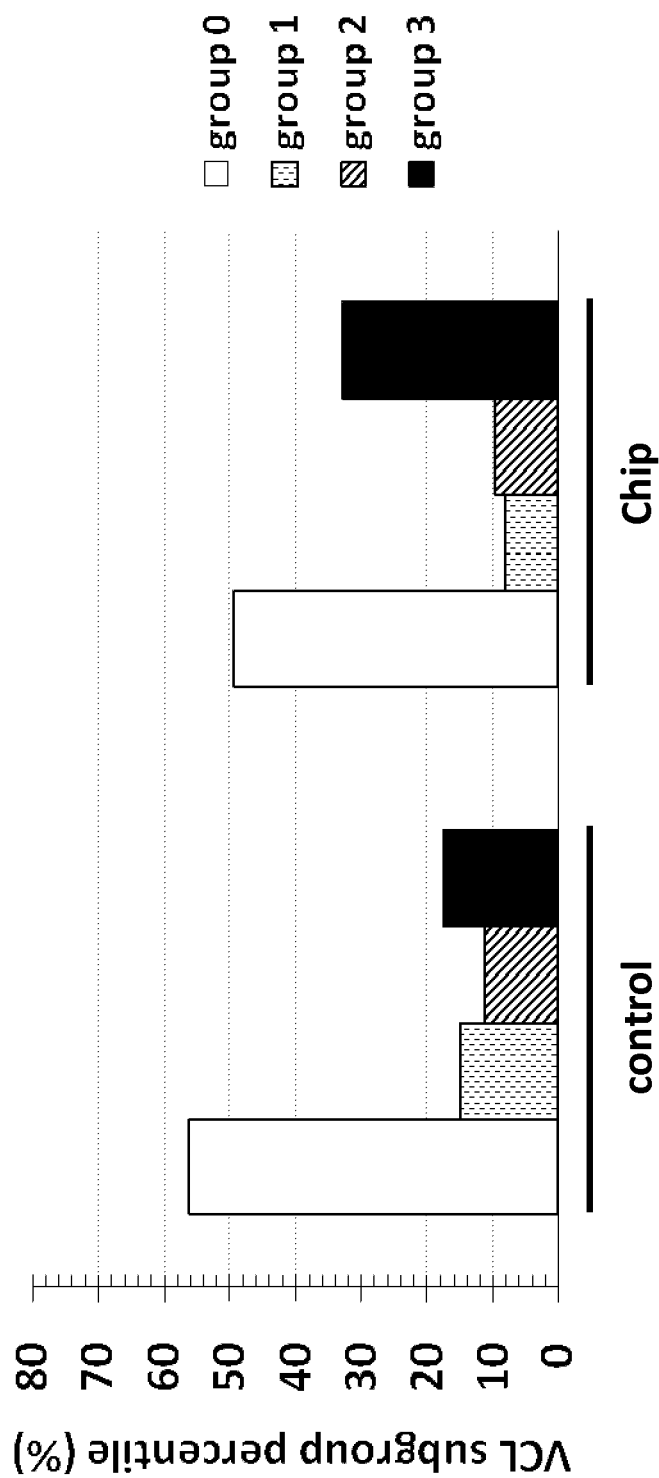
FIG. 11 shows the acquiring results of the human sperms with concentration of $45 \times 10^6$ sperms/ml, using the microfluidic chip of the invention in combination with activating agent of the invention.
Figure 12:
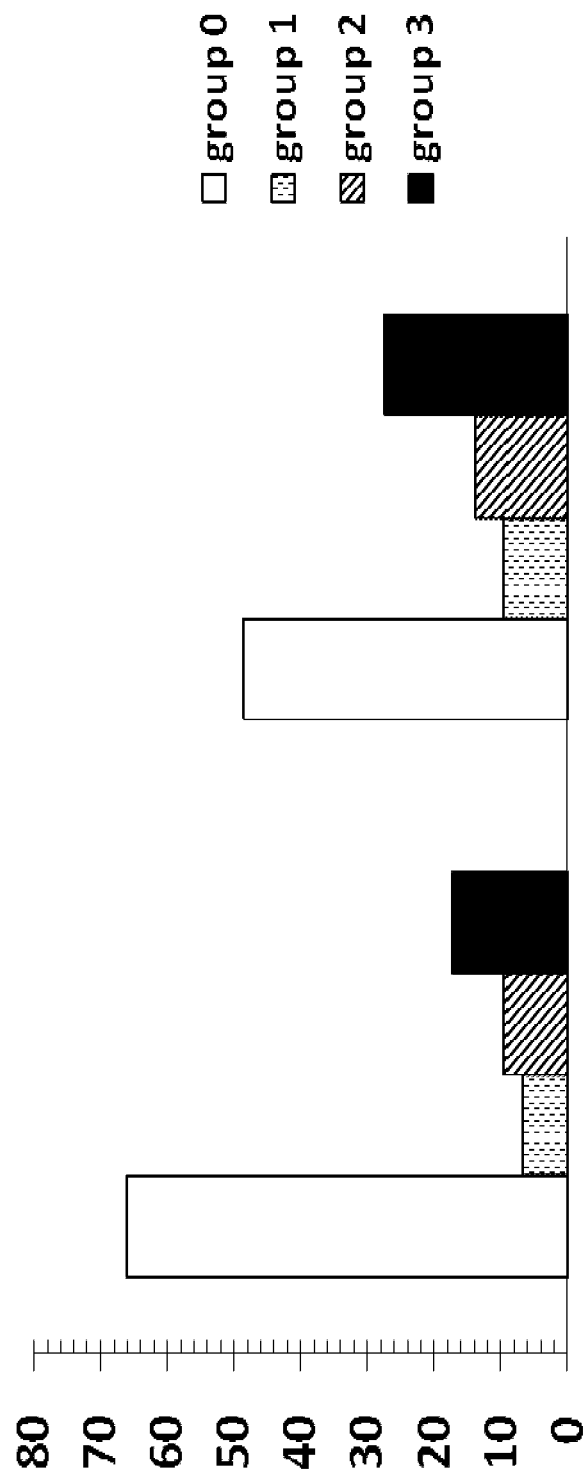
FIG. 12 shows the acquiring results of the human sperms with concentration of $10 \times 10^6$ sperms/ml, using the microfluidic chip of the invention in combination with activating agent of the invention.

Acquiring of Human Sperms Using Microfluidic Chip of the Invention in Combination with Activating Agent of the Invention Semen sample with high concentrations ($60 \times 10^6$ sperms/ml and $45 \times 10^6$ sperms/ml) and low concentration ($10 \times 10^6$ sperms/ml) were obtained from humans. The centrifugation and treatment of samples are the same as mentioned above. The resulting samples were treated with the activating agent of the invention (i.e., pentoxifylline density adjusted in Hans-F10) and then performing high motility sperm acquiring assay as mentioned above. The results are shown in FIGS. 10, 11 and 12 for the samples with concentrations of $60 \times 10^6$ sperms/ml, $45 \times 10^6$ sperms/ml and $10 \times 10^6$ sperms/ml, respectively. For the semen sample with $60 \times 10^6$ sperms/ml, the G3 group of sperms increases from 51% to 73% and the G2 group of sperms reduces from 15% to 11%. For the semen sample with $45 \times 10^6$ sperms/ml, the G3 group of sperms increases from 18% to 36% and the G2 group of sperms reduces from 11% to 9%. For the semen sample with $10 \times 10^6$ sperms/ml, the G3 group of sperms increases from 17% to 28% and the G2 group of sperms increases from 11% to 14%. As a result, the concentration of G2 and G3 sperms increases from $2.7 \times 10^4$ sperms/μl to 4.2 sperms/μl.

Acquiring of Pig Sperms Using Microfluidic Chip of the Invention

The pig sperms are classified as the following three grades according to their curvilinear velocity (VCL).

Group 1 (G1): VCL<120 μm/s;
Group 2 (G2): VCL being 120-180 μm/s;
Group 3 (G3): VCL>180 μm/s.

Figure 13:
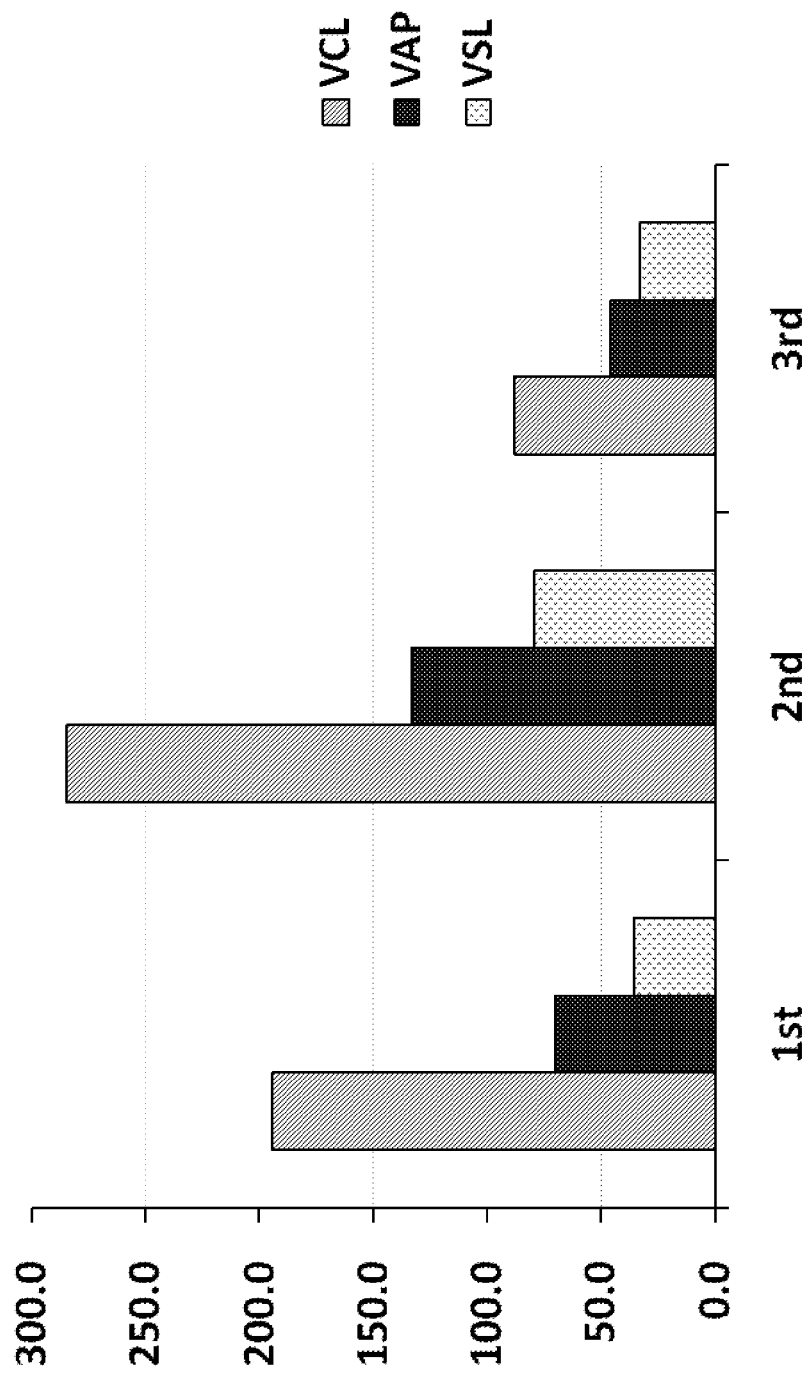
FIG. 13 shows the acquiring results of the pig sperms with concentration of $3 \times 10^8$ sperms/ml, using the microfluidic chip of the invention.

Semen sample with low concentration of $1 \times 10^6$ sperms/ml was obtained from pig. The steps of centrifugation, treatment and sperm acquiring assay are similar to those used in human sample but are appropriately modified to be suitable for pig sample. The results are shown in FIG. 13. The VCL of the acquired sperms are higher than 250 μm/s, proving that the chip of the invention can isolate subpopulations of sperms with different velocities.

Acquiring of Pig Sperms Using Microfluidic Chip of the Invention in Combination with Activating Agent of the Invention Semen sample with low concentration of $3 \times 10^8$ sperms/ml was obtained from pig. 1 ml of 90% Percoll™ (GE Healthcare) was added to a microcentrifuge and then 1 ml of 65% Percoll™ and 1 ml of 40% Percoll™ were in turn added to the tube. 3 ml of the semen sample was added to the tube and centrifugated at 900 g for 20 minutes. The pellet was taken and placed to an eppendorf. 1 ml of dilution solution was added to the eppendorf and then centrifugated at 500 g for 8 minutes. The supernatant was removed. 1 ml of dilution solution was added to the eppendorf and then centrifugated at 500 g for 8 minutes. The supernatant was removed and the pellet was solved and diluted to the concentration of $1 \times 10^6$ sperms/ml. The resulting samples were treated with the activating agent of the invention (i.e., pentoxifylline density adjusted in Hans-F10) and then performing sperm acquiring assay as mentioned above. The results show that after treatment, high than 60% acquiring rate can be reached.

Example 2 Collection of Motile Sperms by Backwash Operation

Figure 14:
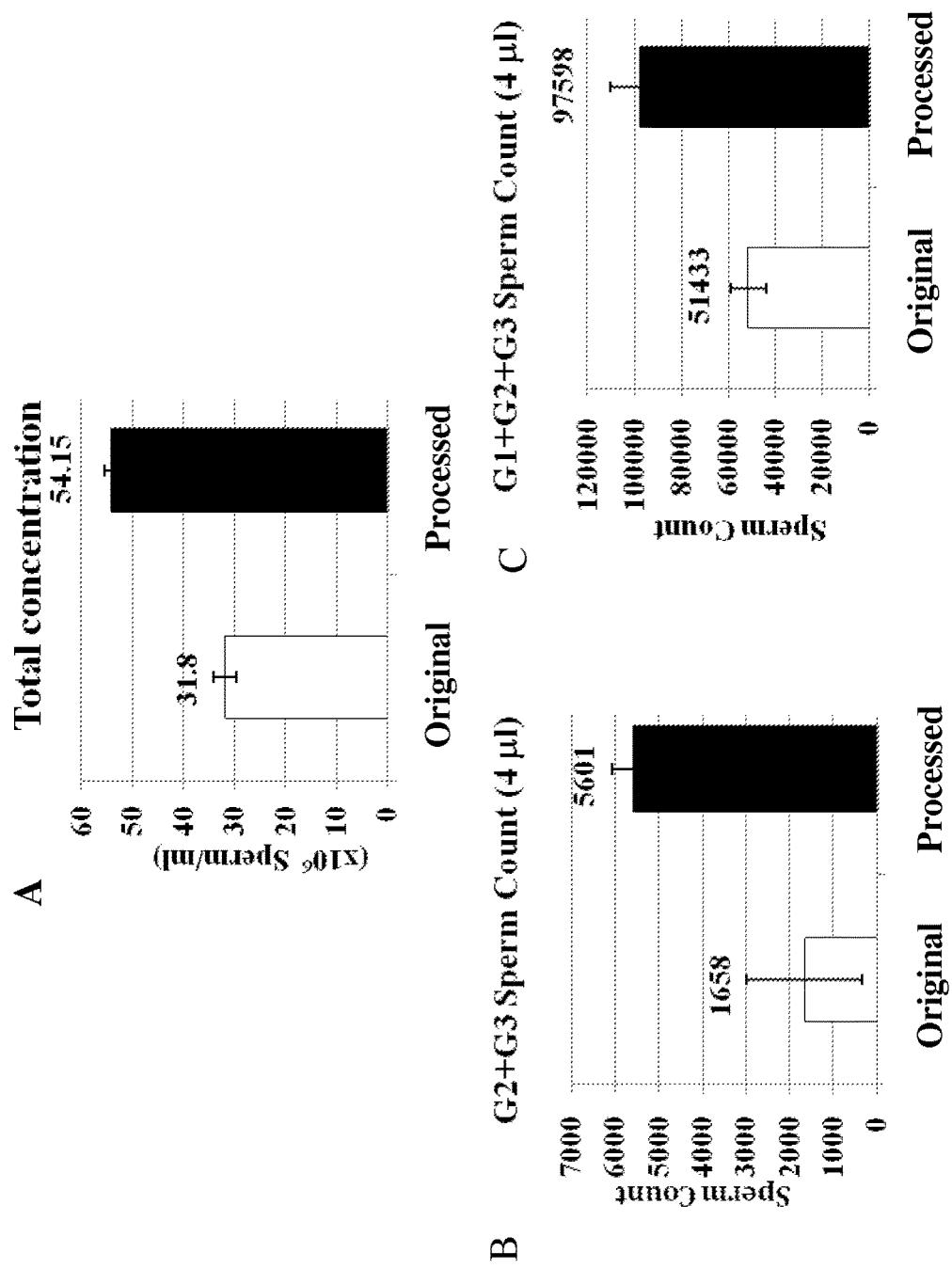
FIGS. 14A, 14B and 14C show the acquiring results through backwash operation of human semen with $31.8 \times 10^6$ sperms/ml, using the microfluidic chip of the invention.

The microfluidic chip as shown in FIG. 2B was used in the backwash operation. The inlet and outlet of the chip were sip up and the chip was put on horizontal operator. 2 μl of Ham's F10 medium was added into outlet to keep flow channel wet. 8 μl of semen with was added into inlet, staying for 10-12 min and then sperm distribution was observed under microscope. The inlet was covered with coverslip and waste was collected from outlet in a new eppendorf. 20 μl of Ham's F10 medium was added into outlet to flush flow channel and the sample was collected from inlet in a new eppendorf. The concentration of original semen is $31.8 \times 10^6$ sperms/ml and the numbers of sperm within G2+G3 group are 1658 sperms (total 4 μl), while those within G1+G2+G3 group are 51433 sperms (total 4 μl) (see FIGS. 14A-14C). After sorting by microfluidic chip, the concentration of sperms is $54.15 \times 10^6$/ml, which concentrated 1.7-fold compared to original semen. Besides, the numbers of sperm within G1+G2+G3 group is 97598 sperms (total 4 μl), which elevates around 1.89-fold. This result indicates sperm sorting by microfluidic chip not only increases overall concentration but also elevates the counts of high motility sperms.

What is claimed is:

1. A microfluidic chip for acquiring sperms with high motility in a sperm sample, which comprises:
   (a) an inlet region at one end of the microfluidic chip for acquiring sperms with high motility in a sperm sample;
   (b) a first flow channel that is in fluidic communication with the inlet region;
   (c) a divergent channel, which is arranged at the downstream of the flow channel and in fluidic communication with the flow channel;
   (c1) a second flow channel arranged at the downstream of the divergent channel;

(c2) a block structure with rounded corners, which is located at the second flow channel; wherein a distance is kept between each side of the block structure and the wall of the channel and wherein the distance ranges from about 100 µm to about 20 µm; and (d) an outlet region at the opposite end of the inlet region of (a) of the microfluidic chip and in fluidic communication with the second flow channel, characterized in that the width of the divergent channel is gradually enlarged starting from that of the flow channel.

2. The microfluidic chip of claim 1, wherein the inlet region is in circle shape and has a diameter ranging from about 0.5 mm to about 2 mm.

3. The microfluidic chip of claim 1, wherein the length of the flow channel ranges from about 5 mm to about 15 mm.

4. The microfluidic chip of claim 1, wherein the angle between the wall of the divergent channel and the wall of the flow channel is about 5 to about 30 degrees.

5. The microfluidic chip of claim 1, wherein the width of the divergent channel increases by more than 1 time to 15 times of that of the flow channel.

6. The microfluidic chip of claim 1, wherein the sperm is obtained from human, pig, horse, dog, sheep, cattle, goat, fish or cat.

7. The microfluidic chip of claim 1, wherein the inlet region is in circle shape and has a diameter ranging from about 0.5 mm to about 4 mm.

8. The microfluidic chip of claim 1, wherein the block structure with rounded corners is dumb-bell structure with rounded corners, a cylinder structure with rounded corners, a cuboid structure with rounded corners, a cube structure with rounded corners or trapezoid bulk structure with rounded corners.

9. The microfluidic chip of claim 1, wherein the block structure with rounded corners is a dumb-bell structure with rounded corners.

10. The microfluidic chip of claim 1, wherein the length of the second flow channel ranges from about 0.5 mm to about 3 mm.

11. The microfluidic chip of claim 1, wherein the outlet region is in circle shape and has a diameter ranging from about 0.5 mm to about 2 mm.

12. The microfluidic chip of claim 1, wherein one or two squeeze flow channel(s) with inlet region is (are) further arranged prior to the divergent channel.

13. The microfluidic chip of claim 1, wherein additional outlets are arranged prior to the divergent channel.

14. The microfluidic chip of claim 13, wherein additional outlets are arranged prior to the divergent channel but after the squish channel(s).

* * * * *